(12) United States Patent
Clay et al.

(10) Patent No.: US 8,003,048 B2
(45) Date of Patent: Aug. 23, 2011

(54) AUTOMATED STANDARDS SAMPLING

(75) Inventors: Brian K. Clay, Westminster, CO (US);
Martin B. Tobias, Longmont, CO (US);
Larry Macklin, Berthoud, CO (US);
Richard D. Godec, Longmont, CO (US); Steve Poirier, Lafayette, CO (US)

(73) Assignee: GE Analytical Instruments, Boulder, CO (US)

( * ) Notice: Subject to any disclaimer, the term of this patent is extended or adjusted under 35 U.S.C. 154(b) by 692 days.

(21) Appl. No.: 11/992,566

(22) PCT Filed: Sep. 30, 2006

(86) PCT No.: PCT/US2006/038254
§ 371 (c)(1),
(2), (4) Date: Mar. 25, 2008

(87) PCT Pub. No.: WO2007/041400
PCT Pub. Date: Apr. 12, 2007

(65) Prior Publication Data
US 2010/0279417 A1    Nov. 4, 2010

Related U.S. Application Data

(60) Provisional application No. 60/723,155, filed on Oct. 3, 2005.

(51) Int. Cl.
*G01N 15/06* (2006.01)
*G01N 35/10* (2006.01)
*G01N 33/18* (2006.01)

(52) U.S. Cl. ........... 422/63; 422/67; 422/68.1; 422/500; 422/509; 422/512; 436/8; 436/43; 436/62; 436/146; 436/180

(58) Field of Classification Search .................... 422/63, 422/68.1, 100, 67, 500, 509, 512; 436/8, 436/43, 62, 146, 180
See application file for complete search history.

(56) References Cited

U.S. PATENT DOCUMENTS

| | | | |
|---|---|---|---|
| 2,817,372 A * | 12/1957 | Barr, Jr. et al. | 141/288 |
| 5,151,184 A * | 9/1992 | Ferkany | 210/514 |
| 5,558,838 A * | 9/1996 | Uffenheimer | 422/100 |
| 5,654,201 A | 8/1997 | Capuano | |
| 5,837,203 A | 11/1998 | Godec | |
| 5,869,006 A | 2/1999 | Fanning | |
| 5,976,468 A | 11/1999 | Godec et al. | |
| 5,980,830 A | 11/1999 | Savage et al. | |
| 5,998,217 A | 12/1999 | Rao et al. | |
| 6,040,186 A | 3/2000 | Lewis et al. | |

(Continued)

*Primary Examiner* — Brian R Gordon
(74) *Attorney, Agent, or Firm* — David Silverstein; Andover-IP-Law

(57) ABSTRACT

An automated standards sampling apparatus (50) and method for using such, apparatus are described. The apparatus can be integrated with a liquid analyzer to form a compact, integrated liquid analysis unit. When used in combination with a specially adapted vial se of standard liquids, the apparatus provides a system for automated, substantially error-free periodic calibration and accuracy verification for an online TOC analyzer (52). The automated standards sampling apparatus of this invention facilitates the easy introduction of known concentrations of standard solutions and "grab" samples into online TOC analyzers to satisfy regulatory compliance, calibration, and validation requirements. The automated standards sampling apparatus of this invention also provides substantially improved reliability, higher productivity and better performance when running the critical and regulatory driven System Suitability Test than does any conventional sampling equipment, and it is likely to find wide use in a variety of industrial applications other than its principal intended use in the pharmaceutical industry.

55 Claims, 5 Drawing Sheets

U.S. PATENT DOCUMENTS

| | | | |
|---|---|---|---|
| 6,054,326 A * | 4/2000 | Dubus | 436/180 |
| 6,135,172 A | 10/2000 | Fere | |
| 6,152,327 A | 11/2000 | Rhine | |
| 6,271,043 B1 | 8/2001 | Godec | |
| 6,330,977 B1 | 12/2001 | Hass | |
| 6,398,956 B1 * | 6/2002 | Coville et al. | 210/321.75 |
| 6,564,655 B1 | 5/2003 | Austen | |
| 6,613,224 B1 | 9/2003 | Strand | |
| 6,649,829 B2 | 11/2003 | Garber | |
| 6,743,202 B2 | 6/2004 | Hirschman | |
| 6,841,774 B1 | 1/2005 | Weiss | |
| 6,887,429 B1 * | 5/2005 | Marshall et al. | 422/81 |
| 7,247,498 B2 * | 7/2007 | Godec et al. | 436/180 |
| 2005/0014271 A1 | 1/2005 | Davis et al. | |

\* cited by examiner

AUTOMATED STANDARDS SAMPLING

CROSS-REFERENCE TO RELATED APPLICATIONS

This application claims benefit of the filing date of international application PCT/US2006/038254, filed Sep. 30, 2006, which claims the benefit of the filing date of U.S. Provisional application Ser. No. 60/723,155 filed Oct. 3, 2005.

FIELD OF THE INVENTION

This invention relates generally to methods and apparatus for facilitating the sampling of packaged standard solutions by online total organic carbon (TOC) analyzers, such as those used in the pharmaceutical industry. Such methods and apparatus improve the productivity and reliability of tests that are performance and/or regulatory-driven, such as in calibration procedures and in carrying out the System Suitability Test. The methods and apparatus of this invention can also generally be applied to improving the productivity of related tests of multiple standard solutions and/or calibration procedures with analyzers of various types that sample liquids for continuous analysis.

BACKGROUND OF THE INVENTION

The United States Pharmacopoeia (USP) and the European Pharmacopoeia (EP) have established various requirements for testing TOC analyzer systems to establish their suitability for use in qualifying pharmaceutical water quality. One of those specific requirements, which relates to the methods and apparatus of this invention, is known as the System Suitability Test (SST). This invention, however, also has general utility in connection with other tests that involve multiple standard solutions and/or calibration procedures that require using multiple standard solutions in analyzers used for continuous process analysis.

The SST consists of multiple analyses of the contents of the different sample vials containing samples $R_w$, $R_s$ and $R_{ss}$ as follows: $R_w$—reagent water that is also used to make the other two standards; $R_s$—a relatively easy-to-oxidize organic compound in the reagent water; and $R_{ss}$—a relatively difficult-to-oxidize organic compound in the reagent water. Each sample vial contains approximately 30 cc of the solution, and multiple measurements are made from each vial. All three vials are analyzed in succession, the analyzer is returned to online operation, and a results report is automatically generated. The present state of the art in this field, (i.e., without this invention), provides for manual insertion and removal of each vial into and from the analyzer during the test, and then manually reconfiguring the hardware (e.g., the operating valves) to return the analyzer to online operation. The analysis of each vial can take from 30 to 40 minutes, resulting in a large time commitment for the user/operator, who must return to the analyzer at least three times to switch from one vial to the next, or to switch from the last vial back to online operation.

A sampling device currently in use, which is generally regarded as the leader among current pharmaceutical TOC analyzers, is called the Integrated Online Sampler (IOS), as described at least in part in U.S. Patent Nos. 5,837,203; 5,976,468; and 6,271,043. This device allows the user to easily switch from online water analysis to grab-sample analysis of sample/calibration vials. The IOS apparatus, however, is a completely passive, non-powered device, which requires manual operation of valves by the user, and does not incorporate any information-management functions. Furthermore, the above referenced patents teach that valving will add contamination resulting in an error when conducting low-level TOC measurement.

Liquid autosamplers have been used with TOC analyzers to provide some level of automation, such as with respect to the ability to sequence through multiple standards or samples without continuous human intervention. Such autosamplers are not commonly used with online analyzers, however, due to cost, adaptation, interface and logistical problems. As one simple example, an online analyzer is usually mounted to a wall in a factory, which would make the interface town autosampler impractical. Since SST protocols are performed relatively infrequently, dedication of an entire autosampler system (which is generally quite expensive) to a given online TOC analyzer is neither economical nor practical.

Representative of pertinent prior art in the fluid sampling field and in related technological areas, such as memory control and venting systems for fluid sampling applications, are the following U.S. patents, each of which is incorporated herein by reference: U.S. Pat. Nos. 5,837,203 (Godec '203); 5,976,468 (Godec '468); 6,271,043 (Godec '043); 5,869,006 (Fanning '006); 6,135,172 (Féré '172); 6,152,327 (Rhine '327); 6,330,977 (Hass '977); 6,564,655 (Austen '655); 6,613,224 (Strand '224); 6,649,829 (Garber '829); 6,743,202 (Hirschman '202); and 6,841,774 (Weiss '774).

For example, the Austen '655 patent is directed to an "Analytical Sampling Device" for automatically taking a known volume of liquid from a source and passing liquid from the sample through a solid phase extraction unit, in combination with information reading and control systems. This system is intended to provide portable equipment for conducting on-site batch groundwater analyses instead of having to freeze and transport groundwater samples to a laboratory for subsequent testing. This invention does not teach or suggest an automated standards sampling apparatus for periodically testing the accuracy of an online analyzer that is continuously monitoring the purity of a flowing liquid according to prescribed testing protocols involving the use of multiple standards solutions.

The Godec '203, Godec '468 and Godec '043 patents, as mentioned previously, are directed to integrated online sampling comprising apparatus and methods for supplying a portion of a fluid stream and, alternately, a fluid of known composition and concentration to an analyzer. The fluid stream is directed along a flow path through a housing containing a sampling needle, which has an inlet in the fluid flow path and an outlet in fluid communication with the analyzer. When desired, a tube or vial containing a known fluid may be inserted into the housing containing the sampling needle, so that the inlet of the sampling needle is in the known fluid whereby the known fluid is supplied to the analyzer. A second needle provides ventilation to the vial of known fluid to prevent the formation of a vacuum as the known fluid is drained from the vial.

Comparable to the present invention, there Godec patents teach online sampling in conjunction with periodic calibration/verification of the associated analyzer unit. In contrast to the present invention, however, the referenced Godec patents do not teach automatically regulating online sampling/analyzer calibration using automated valves, memory storage devices, meeting standards protocols requiring delivery of a controlled sequence of multiple and different standard solutions to the analyzer, automatic monitoring of the standards being used and associated information recording, or using a keyed vial set assembly to eliminate orientation errors when inserting a vial set into the sampling apparatus.

The Fanning '006 patent pertains to a device that fills wells of "cards" and then optically analyzes each well in multiple cards. This device is especially designed to fill, incubate and analyze microbiological samples. The device is not used to calibrate or verify performance of an analyzer. It does not provide a method for removing fluid from the cards but rather performs optical analyses of the contents without removing them from the card. This invention, however, does use a "machine-readable memory storage device" to keep track of the cards within the machine. Bar codes are used on the individual cards, and sets of cards are kept in "cassettes" which use "memory buttons" or "touch buttons" (made by Dallas Semiconductor) to track all the cards in the cassette. This apparatus also provides for automated dilution of samples. It does not, however, relate to on-line sampling.

The Hass '977 patent teaches a medical application for an electronic token system (using "iButtons®" or some equivalent physical realization of the tokens) wherein each token could be used to identify the liquid contents of a single tube sampled by a syringe. In medical applications, the sampled liquid might be blood or therapeutic drugs. This patent also describes how a computer could be used to communicate with the tokens via an RS-232 port, for example to acquire information about the contents of the tubes. However, this invention does not elaborate further on possible uses of such electronic tokens to identify fluid samples (singly or in aggregate); and, in particular, the patent does not teach or suggest an automated standards sampling apparatus for periodically testing the accuracy of an online analyzer that is continuously monitoring the purity of a flowing liquid according to prescribed testing protocols involving the use of multiple standards solutions.

The Strand '224 patent describes a liquid chromatography column that has a built-in memory storage device to identify the column for a specific analytical method. Such applications include the validation of the data on the memory storage device during the manufacture of a cartridge. This patent, however, does not relate to multiple samples or, in this particular case, to multiple columns. The patent does mention encryption of the data stored in the cartridge, but it does not pertain to on-line sampling or calibration applications. In essence, this patent teaches providing a "smart" component for an analysis system rather than providing a "smart" set of analytes.

The Garber '829 patent describes RFID-outfitted fluid couplings. The "smart" couplings can be connected, and, if they are intended to be compatible with the flow of fluid, they can be enabled (by a solenoid valve or pump, for example). This patent, however, does not pertain to on-line sampling, calibration, one-time-use standards, or a single memory storage device identifying the contents of multiple standards.

The Garber '829 patent also teaches about use of a short-range wireless communication system built into mechanically mating fluid couplings. Such system can inform a fluid control device about whether or not the fluid couplings are matched to insure that the fluid would be transmitted only if it was judged to be acceptable in some sense, such as in composition or according to expiration date. However this invention teaches exclusively about the use of wireless communication means (such as RFD modules) to ensure that a mismatch will be sensed remotely before the fluid coupling is completed. This patent does not teach or suggest about the use of a direct electrical connection between halves of the coupling, made after the fluid coupling has been completed, as in the present invention. Furthermore, the Garber '829 patent does not teach or suggest an automated standards sampling apparatus for periodically testing the accuracy of an online analyzer that is continuously monitoring the purity of a flowing liquid according to prescribed testing protocols involving the use of multiple standards solutions.

The Hirschman '202 patent relates to syringes for injecting fluid, such as contrast agents, into human subjects. The syringes of this invention are equipped with memory storage devices that can be programmed to hold information about the contents of a syringe, such as volume available, flow rate, pressure, and limits of piston travel. The "smart" syringe would be placed in an injector, which reads the information from the syringe's memory storage device and delivers the contents in accordance with the data. This patent, however, does not relate to on-line sampling applications.

The Weiss '774 patent describes a multi-stream valve for a mass spectrometer inlet. The valve selects flowing streams of gaseous analyte. This patent, however, does not relate to liquid sampling or memory storage devices.

The Féré '172 patent pertains entirely to the design of a needle for piercing rubber stoppers or septa in the tops of test tubes containing samples to be extracted, especially Vacutainer-style (Vacutainer is a trade name of the BD Diagnostics Corporation), in which a vacuum is inside the tube. The needle design provides a novel shape to prevent coring of the septum and plugging of the needle. The needle of this patent has grooves cut into its exterior, which grooves act as integral "vent needles" which relieve pressure differences once the needle is fully inserted into the test tube. This needle design is used to remove, for example, blood samples from a test tube with sub-ambient pressure inside. This patent, however, does not pertain to on-line sampling, memory storage devices, stream selection or calibration.

The Rhine '327 patent pertains only to the delivery of reagents, chemicals, detergents and the like—not to the delivery of calibration standards. This patent discloses a novel sealing mechanism that allows air exchange into a sealed container holding a liquid without liquid leakage. This patent does not, however, teach anything about memory storage devices or on-line sampling of a liquid stream requiring analysis.

In contrast to a conventional liquid autosampler, the automated standards sampling apparatus of this invention provides automated information management features, can readily switch between vial sampling and online sampling, and is fully integrated to the TOC analyzer to perform all liquid sampling functions. While extra hardware and software might, at some considerable expense, be added to a conventional autosampler system to provide, for example, bar code scanning of vial information and automated valving to switch back to online measurements, the resulting system would still lack a high and coherent degree of system integration as is required for convenient and reliable System Suitability Testing in an industrial factory environment, for example.

Among other advantages, the present invention reduces the operator time commitment to a single interaction which sets into motion the entire multi-step SST, at the conclusion of which (if the SST is successfully passed) the analyzer is automatically returned to online analysis, thereby minimizing the amount of time during which the analyzer is off-line and the process liquid quality is not being monitored.

In addition to human and equipment timesavings, this invention also improves the reliability of System Suitability Testing. Without this invention, the user must verify that each standard solution is viable—i.e., that its expiration date has not yet passed. The user must also transcribe certain information from the vials to written report records of the test, ensure that the proper set of standards is being used for the test, and ensure that the standards are analyzed in the proper sequence. These potential sources of error in performing the conventional SST can result in a failed SST, at which point the entire process must be repeated. In contrast, this invention automatically transfers vial information to the analyzer, and software associated with the analyzer ensures the proper sequencing of the vials for analysis and prevents out-of-date standards from being analyzed.

The invention also incorporates automated valving, preferably fabricated using substantially inert materials, that, unlike earlier sampler valving designs, does not introduce levels of contamination into samples being analyzed sufficiently high to interfere with accurate low-level TOC measurement.

The improved reliability, inertness of materials, convenience and productivity of the present invention also apply to oilier tests that may be performed with multiple standards, including tests for Accuracy/Precision/Verification, Calibration, and Linearity. In each case, using the present invention, the TOC analyzer is given the vial information electronically, which thereby ensures proper sequencing of the vials and recording of information about the vials.

OBJECTS OF THE INVENTION

Accordingly, a principal object of the present invention is to provide methods and related automated standards sampling apparatus for switching a TOC analyzer from an online sampling mode to processing several standard solutions automatically, and then returning the TOC analyzer to the online sampling mode.

Another object of the present invention is to provide a system of managing information for individual standards and sets of standards, and to minimize potential errors that might be introduced as a result of manual transcription of identification and other such information from labels on sample vials to written reports, analyzing standards that have expired, and/or analyzing vial sets in an improper sequence for a given protocol.

Still another object of this invention is to provide methods and related apparatus whereby a "grab" sample may be taken from any source for analysis, wherein such "grab" sampling is fully integrated with an automated standards sampling system for switching a TOC analyzer from an online sampling mode to processing several standard solutions automatically, and then returning the TOC analyzer to the online sampling mode.

Yet another object of this invention is to provide a keyed vial set assembly adapted to mate with the automated standards sampling apparatus of this invention whereby a physical feature of the "keyed" assembly, e.g., enlarged spacing between two adjacent vials (such as between the first and second vials) prevents mistakes such as inserting the vial set assembly backwards.

Still another object of this invention is to provide an automated valving system, preferably fabricated of substantially inert materials, to further eliminate or at least minimize introduction of contamination into the sampling systems of this invention.

These and other objects and advantages of this invention will be apparent from the following detailed description with reference to the attached drawings.

SUMMARY OF THE INVENTION

The automated standards sampling apparatus which is a preferred embodiment of the present invention comprises an integrated sampling system in combination with an online TOC analyzer. An external view of such a compact, integrated system is shown in FIG. 5. As shown schematically in FIGS. 6 and 7, individual vials can be sampled, or sets of vials that have been prepackaged and contain electronic information can be automatically sampled according to the System Suitability Test or another such sampling protocol. During manufacture of vial sets for use with the sampling system of this invention, multiple quality-assurance steps may be taken to ensure that the electronic data programmed into the memory storage system, for example an iButton®-based system or other non-volatile memory storage device, is accurate. The physical design of a preferred embodiment of a vial set for use in this invention is such that improper insertion of a standard vial by a user into the automated standards sampling apparatus of this invention is prevented.

In general, to perform a given protocol in accordance with this invention, a user directs the TOC analyzer to begin the desired testing protocol, and then the user inserts a suitable vial set into the associated sampling apparatus. No additional user interaction with the sampling apparatus is required. The analyzer and the automated standards sampling apparatus act in conceit to analyze each of die vials' contents, in the proper sequence, and while also ensuring vial viability, and then (if the system passes the testing protocol) to return to monitoring online liquid quality, if the user has selected that option beforehand. The user can also instinct the system to output a formal report of the test results) which explicitly lists the details of each of the standard vials that have been analyzed, including, for example, manufacturer's lot or batch designator, expiration date, vial contents and results of the analyses. After vial sampling is complete, the user should, at a convenient time, ordinarily remove the vial or vial set from connection to the sampling apparatus to limit the potential for biological growth to occur near the sampling needles.

DETAILED DESCRIPTION OF PREFERRED EMBODIMENTS

Figure 1:
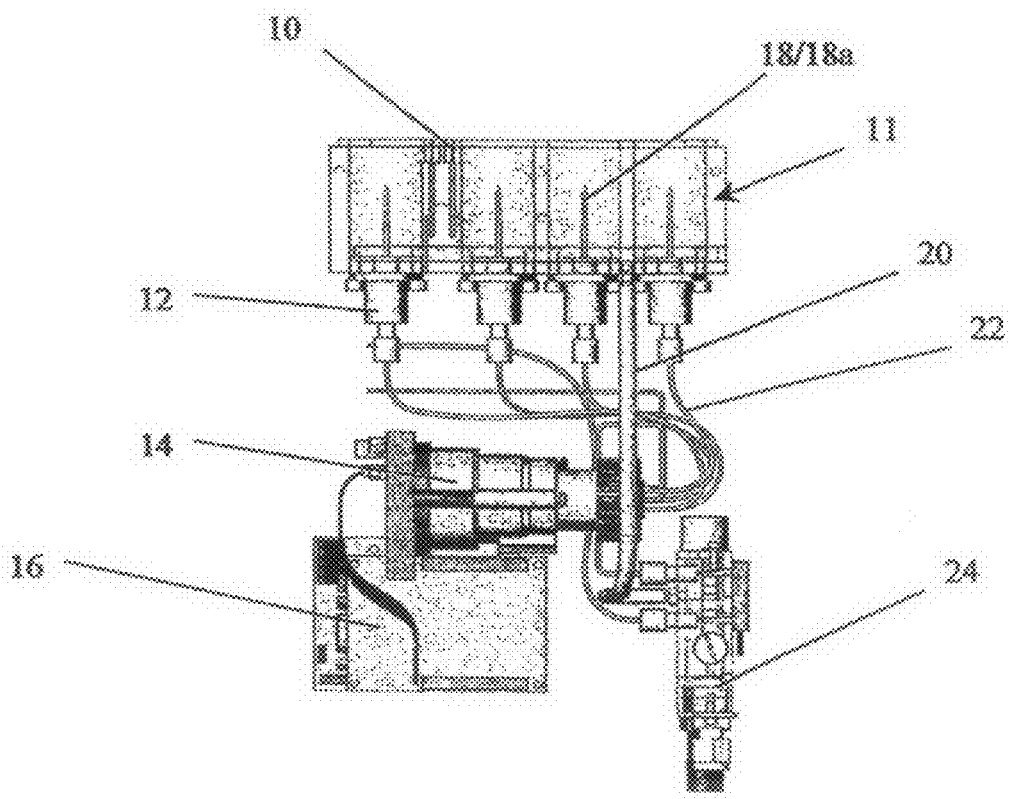
FIG. 1 is a schematic front view of a preferred embodiment of an automated standards sampling apparatus according to this invention showing the key functional components.

FIG. 1 is a schematic front view of one preferred embodiment of an automated standards sampling apparatus according to this invention. The sampling apparatus as shown in FIG. 1 includes a vial set receiving structure 11 sized, shaped, spaced and oriented to receive a standards vial set as discussed hereinafter. In the embodiment illustrated in FIG. 1, the vial set receiving structure comprises a plurality of interconnected, open-ended tubular elements or vial chambers (reference numeral 26 in FIG. 2), each for receiving a standards vial, oriented in a straight line and such that their respective central axes are substantially parallel.

The spacing between adjacent vial chambers of the vial set receiving structure is, preferably, not completely uniform. Thus, as seen in FIG. 1, the spacing between the first (left end) vial chamber and the second vial chamber (second to left) is greater than the spacing between the second and the third vial chambers and also greater than the spacing between the third and the fourth (right end) vial chambers. This configuration of the vial chambers provides a physical "key" feature to insure that a vial set is correctly inserted into the vial set receiving structure.

The top ends of the vial chambers remain open to receive the plurality of vials that constitute a standards vial set. The number of vial chambers should be at least as great as the number of vials in a vial set intended for use with this apparatus. The bottom end of each vial chamber is fitted with a needle holder assembly 12 that holds a sample needle 18 and a vent needle 18a in a coaxial configuration oriented substantially vertically and having a tip portion configured to pierce a piercable septum that seals an end of each standards vial, as discussed further hereinafter.

A contact element 10, such as an electrical contact, designed to provide an interface with an electronic memory storage device or a comparable element having information perceiving, storage, and communicating capability, is also located in the vial set receiving structure as shown in FIG. 1 in the intentionally enlarged space between the first and second vial chambers. In a preferred invention embodiment, the a commercially available iButton® element, which would be incorporated into the standards vial set as described hereinafter.

Sample needle tubing 22 extends between a lower outlet end of each sample needle 18 and an inlet to a central or hub valve such as stream selection valve 14. From stream selection valve 14, a fluid sample is passed to the online sampling block 24, as described further hereinafter.

FIG. 1 also shows an assembly 16 comprising an interface board, a single board computer, and an interface element connecting the interface board to the electronic memory storage device of a vial set assembly when the vial set assembly is positioned in the vial set receiving structure. The interface board facilitates downloading and decrypting relevant information from the vial set and communicating such information to the TOC analyzer, as hereinafter described.

Figure 2:
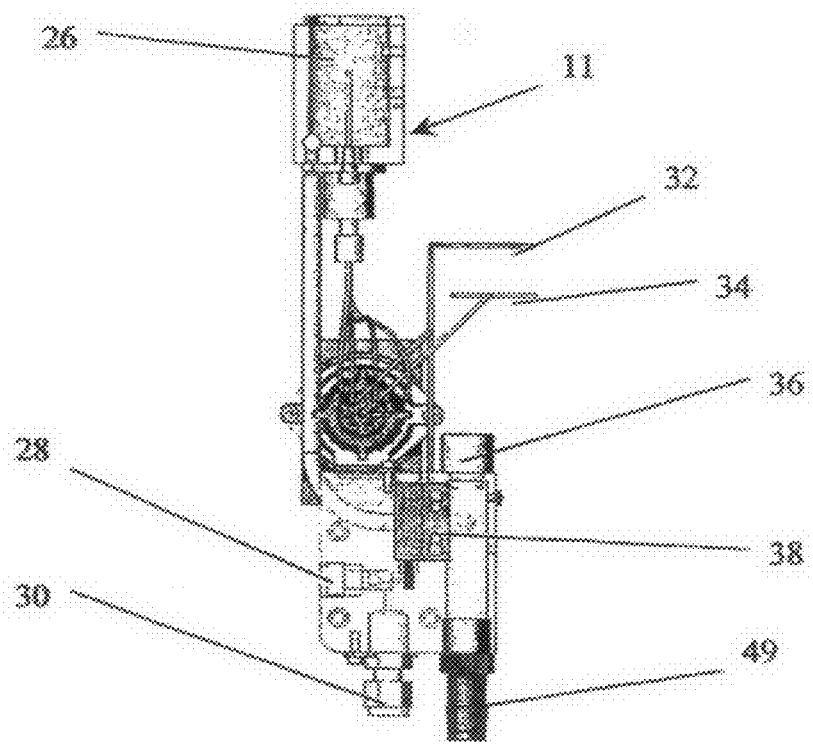
FIG. 2 is a schematic right-side view of the same assembly shown in FIG. 1.

The function of vial chamber drain 20 as shown in FIG. 1 is to pass any vial contents that might accidentally spill to a waste/drain connector 49, as shown in FIG. 2.

Figure 3A:
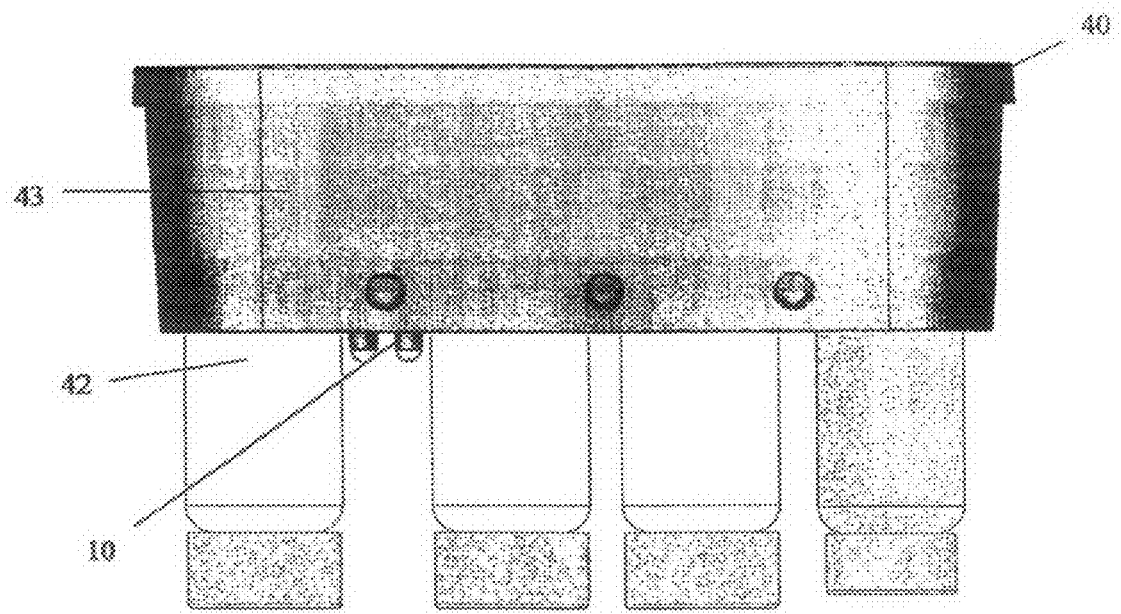
FIG. 3A schematically illustrates a preferred embodiment of a "keyed" vial set assembly (with enlarged spacing between the first and second vials of the set) according to this invention, this assembly being adapted for use with an automated standards sampling apparatus such as that shown in FIGS. 1 and 2.
Figure 3B:
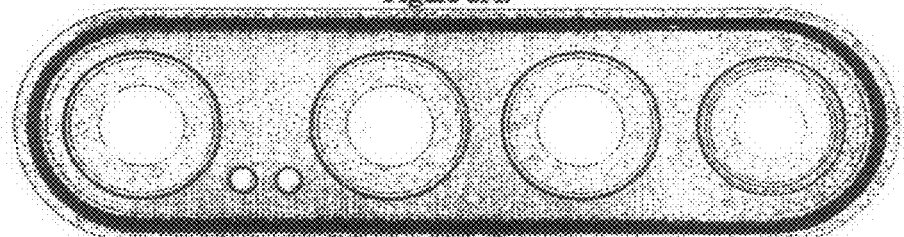
FIG. 3B schematically illustrates a bottom view of the vial set assembly seen in FIG. 3A specifically showing the pier-cable septum at one end of each standards vial.
Figure 4:
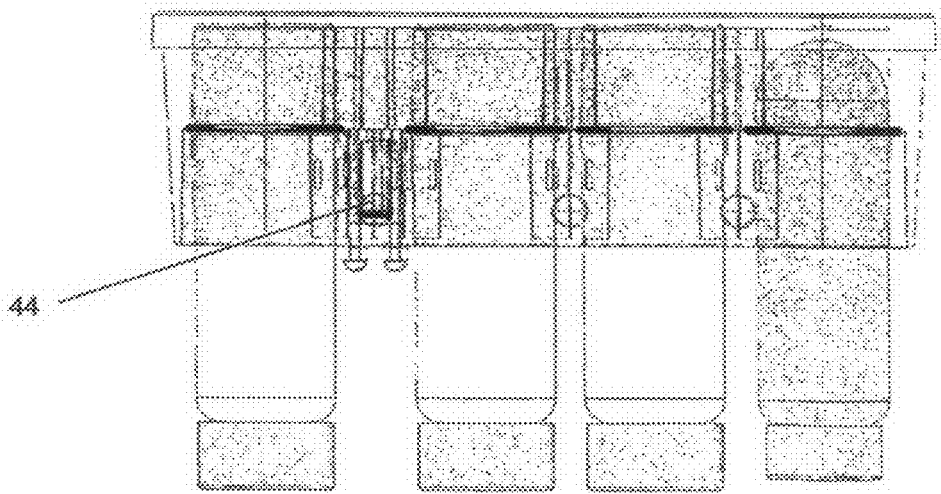
FIG. 4 schematically illustrates a similar view of the vial set assembly as shown in FIG. 3A, but with the front portion of the vial set housing—for example, comprising two injection-molded (typically plastic) shells—removed to expose the interior region and to illustrate the upper ends of the several vials, how the vials engage with the housing, and the positioning of the memory storage device.

FIG. 2 is a schematic right-side view of the assembly shown in FIG. 1, which shows the right-end vial chamber 26 (which receives the fourth of the four standards vials as shown in FIGS. 3A, 3B and 4). FIG. 2 also better illustrates certain additional elements of the automated standards sampling apparatus of this invention. Thus, FIG. 2 shows the analyzer inlet line 34, the waste line 32 for waste coming from the analyzer, and the vent drain connector 36. Also seen in FIG. 2 is the (preferably magnetic) flow switch 38, the flow-controlling needle valve 28, the online sample inlet 30, and the waste/drain connector 49, the purposes and functions of which are explained hereinafter.

One or more assembled vial set(s) in accordance with this invention, such as that shown in FIGS. 3A, 3B, and 4, contains all of the standard solutions required to perform a given protocol—for example, a System Suitability Test. The standards vials are permanently contained in the vial set assembly 40 (comprising the vials and a vial set housing) to guarantee sequence integrity. All relevant information pertaining to each of the individual standards vials, and information pertaining to the set as a whole, is preferably stored on a suitable electronic memory storage device which is incorporated into the vial set assembly 40. In alternative invention embodiments, however, other types of electronic and/or magnetic and/or light reading, coding, sensing or other information-perceiving and communicating systems, for example bar coding in combination with a bar code reader, could be substituted for the memory storage device in this invention. In one preferred embodiment of this invention, the memory storage device is a commercially available device which is known as an iButton®—a robust package containing non-volatile random access memory (NVRAM) which is manufactured by Dallas Semiconductor.

In another preferred embodiment of this invention, the vial set assembly 40 is "keyed" to the automated standards sampling apparatus by means of a physical feature, such as irregular spacing between the vials, to prevent an orientation or similar error during insertion of a vial set assembly into the sampling apparatus. For example, as shown in FIGS. 1, 3A, 3B and 4, the spacing between vials 1 and 2 can be made larger than the spacing between other adjacent vials to prevent accidentally inserting the vial set into the sampling apparatus backwards (i.e., with vial 4 in the position where vial 1 should be).

The iButton® memory storage device provides significant benefits for a user relative to the practice of this invention. It can be programmed to contain information about an entire Vial Set (e.g., the information shown below in Table 1) as well as information about each individual vial within the Vial Set (e.g., the information shown below in Table 2).

TABLE 1

| Vial Set Information |
| --- |
| Part number. |
| The name of the vial set. |
| The expiration date for the vial set. |

TABLE 2

Individual Vial Information

Part number.
Lot number.
A field indicating the type of standard.
The expiration date for this particular vial.
The concentration of the solution in the vial.

When a vial set equipped with an electronic memory storage device, such as the iButton®, is inserted into an integrated analysis system in accordance with this invention, the analyzer unit of the system reads the information from the iButton® into the analyzer. This allows the analyzer to verify that the proper vial set has been installed for the selected protocol. It can also check the expiration date and can warn the user if any of the vials are beyond an expiration date. This checking/verification process prevents wasted time and money, which might otherwise occur if the wrong vial set were installed.

The information from the iButton® is stored with the results of the analysis in the analyzer. Subsequent reports from the analyzer can display the results and the information obtained from the iButton® This allows independent reviewers to verify that the proper standards were used in producing the data for the report. The data contained in the iButton® is encrypted so the analyzer can verify its validity. This system also provides a traceable link from the factory, to the analyzer, and finally to the report.

Figure 6:
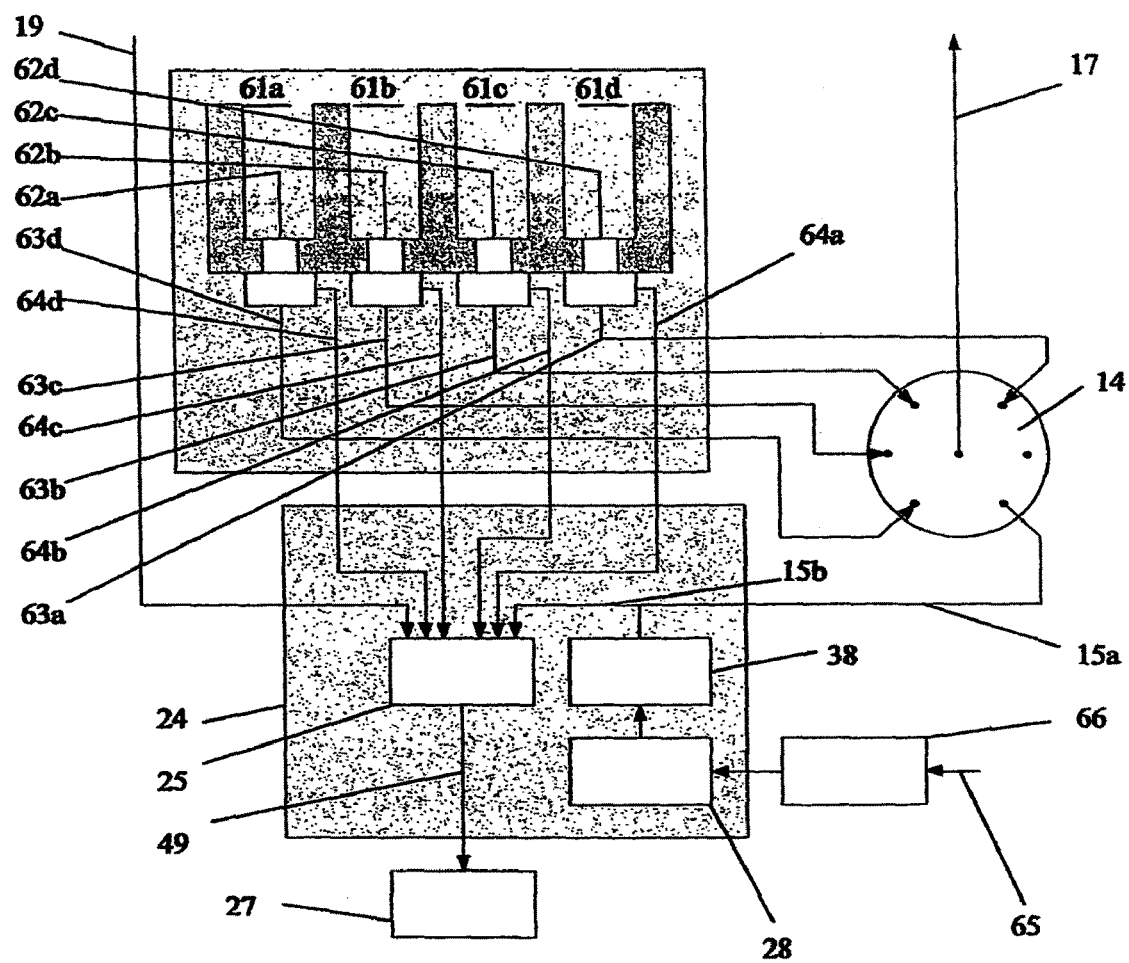
FIG. 6 is a schematic diagram representative of the fluidic circuit within an automated standards sampling apparatus according to this invention.

FIG. 6 is a schematic diagram that is representative of a fluidic circuit within an automated standards sampling apparatus according to this invention to show fluid flow pathways in greater detail than was possible in FIGS. 1 and 2. FIG. 6 schematically illustrates four vial chambers 61a, 61b, 61c and 61d, which generally correspond to the vial chambers 26 in FIGS. 1 and 2, except that FIG. 6 does not show irregular spacing between these chambers because such a physical "key" feature is not relevant to a fluid flow diagram.

Each of the vial chambers 61a, 61b, 61c and 61d has a coaxial sample and vent needle combination (generally corresponding to 18/18a in FIG. 1), i.e., 62a, 62b, 62c and 62d, respectively, positioned centrally inside the vial chamber so as to pierce the piercable septum of the corresponding standards vial when a vial set assembly is put in place. Fluid sample lines 63a, 63b, 63c and 63d, respectively coming from needles 62a, 62b, 62c and 62d, connect respectively to one of the multiple fluid inlets of the stream selection valve (14 in FIG. 1). Fluid waste lines 64a, 64b, 64c and 64d, respectively coming from the bottoms of vial chambers 61a, 61b, 61c and 61d, connect with a drain chamber 25 located within or adjacent to the online sampling block (24 in FIG. 1); and, from drain chamber 25 the waste fluid is passed by a waste/drain connector 49 to a waste drain 27. An online fluid line 15a connects the stream selection valve 14 and the sampling block 24. A sample fluid line 17 carries a fluid sample from the stream selection valve 14 to an inlet of an associated TOC analyzer (not shown in FIG. 6).

During ordinary operation, an online fluid sample is continuously withdrawn from a flowing stream of primary fluid, passed by means of an online sample inlet 65 through a filter 66, into the online sampling block 24, through a needle valve 28 within sampling block 24, then to a flow controller or switch 38. From flow controller 38, the online-fluid sample is passed via line 15a to stream selection valve 14, and thence via line 17 to the TOC analyzer for continuous online monitoring of the primary fluid. Excess primary fluid (that not required by the TOC analyzer) flows through waste line 15b to drain chamber 25, and then through waste/drain connector 49 to waste drain 27.

During a periodic calibration of the TOC analyzer, however, the online fluid sample is directed from flow controller 38 through waste line 15b to drain chamber 25 instead of to stream selection valve 14. During such a calibration or system suitability test, in place of the online fluid sample, standard samples are withdrawn sequentially from the set of standards vials positioned in the vial chambers 61a, 61b, 61c and 61d, and passed via stream selection valve 14 to the associated TOC analyzer. At the conclusion of such a calibration or system suitability test, the flow of online fluid sample from flow controller 38 to stream selection valve 14 is resumed. Using programmable software according to this invention, all of this sequence of steps can automatically be carried out on a regular basis, while simultaneously recording all pertinent information.

Figure 5:
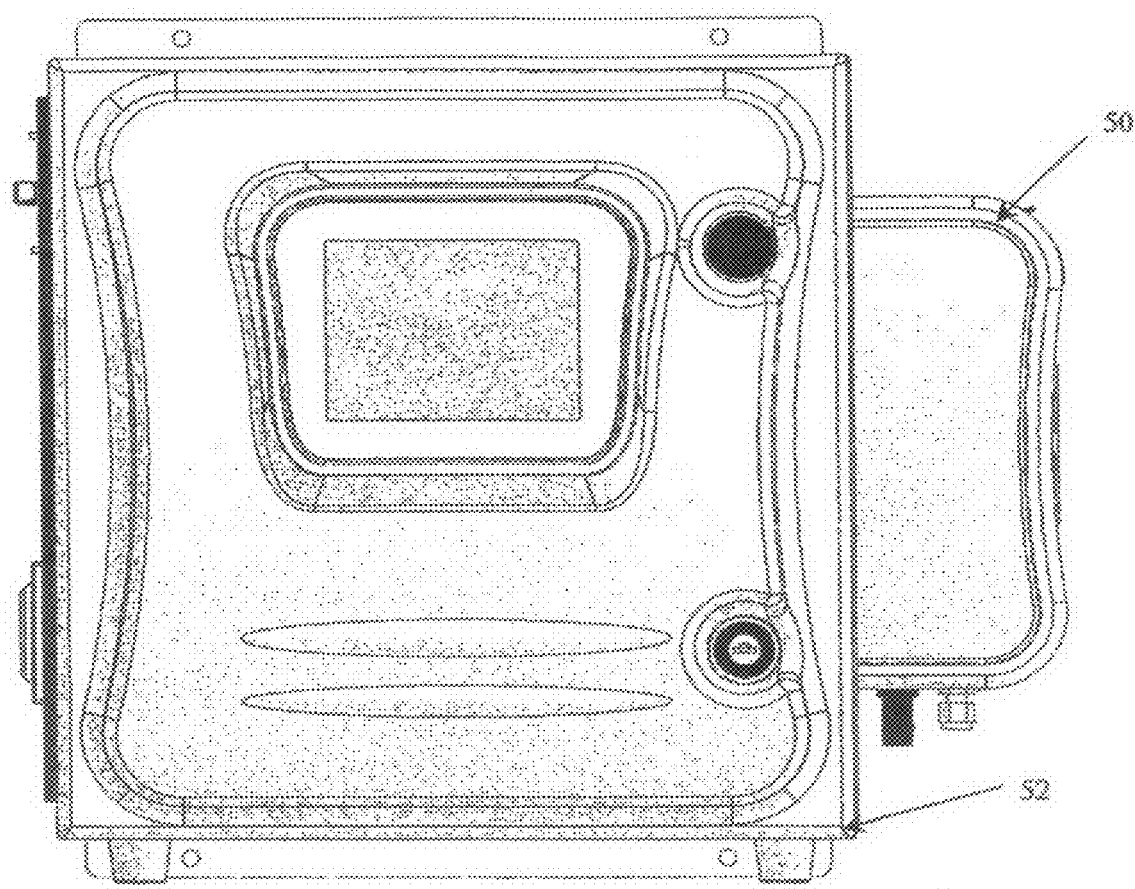
FIG. 5 schematically illustrates a preferred invention embodiment wherein an automated standards sampling apparatus 50 according to this invention is integrated with an online TOC analyzer 52 to form a compact analysis system as a single, easily transportable unit for use in an industrial manufacturing environment.
Figure 7:
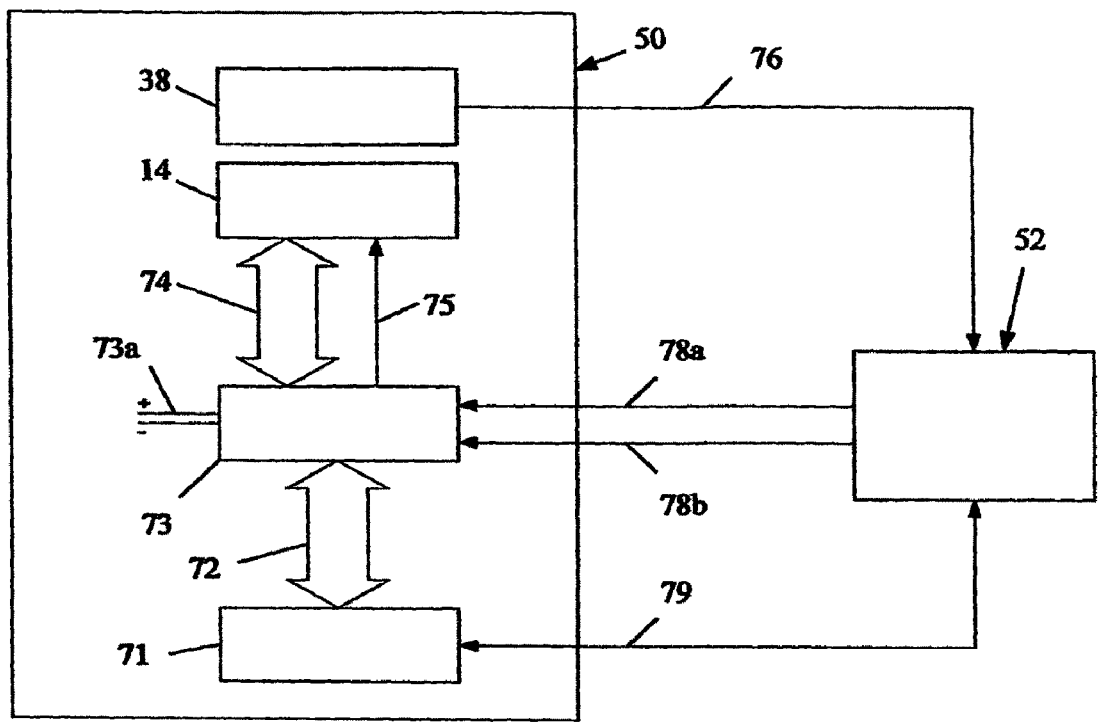
FIG. 7 is a schematic diagram representative of the electrical interconnections between components of an automated standards sampling apparatus according to this invention, and also between the automated standards sampling apparatus and an associated online TOC analyzer, for example as in the integrated analysis system unit shown in FIG. 5.

FIG. 7 is a schematic diagram that is representative of an electrical circuit interconnecting components of an automated standards sampling apparatus according to this invention to show electrical interconnections in greater detail than was possible in FIGS. 1 and 2. FIG. 7 schematically illustrates the key electrical connections between various components of an automated standards sampling apparatus (50 in FIG. 5) of this invention, and also between the sampling apparatus 50 and an associated TOC analyzer (52 in FIG. 5).

As seen in FIG. 7, a single board computer 71 is electrically connected by means of a communications bus 72 to an interface board 73 (in FIG. 1, these three elements are combined in a single package identified by reference numeral 16). The interface board 73 includes electrical wires 73a for establishing an electrical connection to the electrical contacts (10 in FIGS. 1 and 3A) of an electronic memory storage device (44 in FIG. 4), preferably the iButton® contacts of an iButton® unit, when a vial set assembly including the memory storage device is positioned in the vial set receiving structure (11 in FIG. 1).

A second communications bus 74 electrically connects interface board 73 to stream selection valve (14 in FIG. 1), and a 24 VDC power line 75 also runs from interface board 73 to stream selection valve 14. The sampling apparatus 50 as depicted in the electrical circuitry illustration of FIG. 7 further shows the flow controller or switch (38 in FIG. 6).

As shown in FIG. 7, there are several electrical connections between the automated standards sampling apparatus 50 and the TOC analyzer 52. A 24 VDC power line 78a and a power-on signal line 78b connect TOC analyzer 50 to interface board 73. Additionally, switch cable line 76 connects flow switch 38 to TOC analyzer 50. Also, an RS-232 cable 79 connects single board computer 71 and TOC analyzer 50. A more detailed description of how these various elements cooperate appears hereinafter.

Thus, in a preferred invention embodiment, a single board computer (SBC) 71, in combination with suitable software designed or adapted to perform the appropriate information reading/storage, sequencing and control operations, which is part of the automated standards sampling apparatus of this invention, is used to process communications between the analyzer 52 and the sampling apparatus 50 (for example, as illustrated by the electronic circuitry shown in FIG. 7). The SBC is responsive to RS-232 commands from the analyzer. The commands are converted to electrical signals and sent to the interface board 73 where they control the hardware components of the sampling apparatus. The SBC can read the iButton® information and command one or more valve/fluid flow control devices of the sampling apparatus, for example the stream selection valve 14 (FIG. 1) to change to a new position. The stream selection valve 14 selects one of the sampling apparatus standards vials or the external water stream as the liquid source for the associated TOC analyzer. Designing customized software or adapting off-the-shelf software to perform the necessary information reading/storage, sequencing and control operations of this invention would be a matter of routine development work for one of ordinary skill in this field working with the teachings of this invention.

When the vial set is inserted into the vial chambers 26 (FIG. 2), the iButton® makes electrical contact by means of an element known as a 1-wire interface to gold-coated, spring-loaded contacts 10 (FIG. 1) that are wired to the interface board (as seen in FIG. 7). This electrical connection enables the TOC analyzer to download and decrypt all of the relevant information from the vial set, through the interface board and SBC 16 (FIG. 1).

As the vials of vial set assembly 40 are inserted into the vial chambers 26 (FIG. 2), sets of coaxial sample and vent needles 18/18a (FIG. 1) pierce the respective septa (as seen in FIG. 3B) sealing the mouths of the several sample vials, thereby forming liquid-tight seals. Pump units within the TOC analyzer draw fluid from the particular vial selected by the position of the rotor in the stream selection valve 14 (FIG. 1), via the sample needle associated with the particular vial. The vent needle associated with the particular vial allows the resulting vacuum within the vial to be relieved, via a conduit connecting to the vent drain connector 36 (FIG. 2).

In the event that one or more of the sample vials' contents accidentally spill into the associated vial chamber 26 (which might occur, for example, if the user had inadvertently loosened one or more of the screw caps that seal the vials), then this fluid is directed through the vial chamber drain 20 (FIG. 1), and it exits the system via the waste/drain connector 49 (FIG. 2). This feature is also useful for draining any liquid that may get into the vial chamber 26 during the course of regular maintenance and cleaning.

During online analysis, sample liquid enters the online sampling block 24 (FIG. 1) via the online sample inlet 30 (FIG. 2). The total flow rate through the online sampling block 24 may be manually adjusted using the flow-controlling needle valve 28 (FIG. 2) or a suitable flow control device. Downstream of valve 28 is a magnetic piston, which rises when liquid is flowing. The flow switch 38 (FIG. 2) detects the presence of the piston in the raised position, indicating that sample liquid is flowing through the system, and this information is used by the TOC analyzer for the benefit of providing warnings as appropriate to the user.

Internal surfaces of the apparatus elements of this invention which come into contact with any sample prior to analysis, such as tubing and valving, are preferably fabricated of substantially inert materials to minimize contamination. For example, tubing, preferably stainless steel tubing, conducts sample liquid from the online sampling block 24 through the stream selection valve 14 and into the analyzer inlet 34. Stainless steel is preferably selected as a material for fabricating tubing, valve components, and the like, for purposes of this invention, for its very low contribution of total organic carbon, inorganic carbon and conductive species to the sample liquid, which is important for accuracy when a TOC analyzer is to be used in highly sensitive and precise applications, for example in pharmaceutical water systems. Plastic tubing may be used, on the other hand, to conduct waste streams out of the system.

The stream selection valve 14 comprises one common port selectively connected to one of five inlet connections, thereby enabling the system to select either one of four sample vials or online liquid for analysis by the TOC analyzer. The valve 14 preferably uses materials selected for extremely low carbon contribution and conductive species contribution to the conducted water under operational wetted conditions.

In still another invention embodiment, it will be apparent to one skilled in this art that the methods and apparatus as described above (and as shown in the drawings) can also be readily adapted and utilized to periodically take a "grab" sample from any source for analysis instead of operating in the online analysis mode or the standards solution analysis mode.

The present invention has been described in detail with reference to preferred embodiments thereof, and although specific terms are employed in describing this invention, they are used and are to be interpreted in a generic and a descriptive sense only and not for purpose of limitation. Accordingly, it will be understood to those of ordinary skill in the art that various changes, substitutions and alterations in form and details may be made without departing from the spirit and scope of the present invention as set forth in the following claims.

Having described the invention, what is claimed is:

1. An automated standards sampling apparatus comprising systems for fluidically and electronically coupling an online flowing liquid sample to an analyzer inlet line that carries fluid to be analyzed to an analyzer, and for alternatively periodically coupling into the apparatus a plurality of standards vials contained in a standards vial assembly so as to individually deliver a portion from each of two or more vials in the standards vial assembly in a predetermined sequence to the analyzer inlet line, or instead to deliver a portion of another liquid to the analyzer inlet line, said systems comprising:

(a) an analyzer inlet line;
  (b) a single functional stream selection element providing a plurality of stream selection fluid inlets, each being in fluid communication with a common interior region of the stream selection element and wherein the interior region of the stream selection element communicates with the analyzer inlet line of part (a);
  (c) an online sample inlet and an associated conduit for flowing an online flowing liquid sample into the apparatus and then to one of the stream selection fluid inlets when the apparatus is operating in an online mode of operation;
  (d) a standards vial receiving assembly comprising a plurality of vial receiving structures each sized and configured to accommodate a vial of a standards vial assembly, said receiving assembly comprising a keying feature that is keyed to a corresponding keying feature of a suitable standards vial assembly that prevents the standards vial assembly from being inserted into the receiving assembly unless the standards vial assembly is adapted to be used with the receiving assembly and is properly positioned for insertion;
  (e) a fluid connection system providing a separate connection from each of two or more standards vials of a standards vial assembly inserted into the receiving assembly to separate stream selection fluid inlets; and,
  (f) a computer information reading and control system capable of operating the fluid connection system so as to deliver either the online liquid sample or instead a sequence of individual portions from two or more standards vials of a properly positioned standards vial assembly to the analyzer inlet line in a predetermined sequence, or, optionally, to periodically deliver another liquid to the analyzer inlet line.

2. An automated standards sampling apparatus according to claim 1 further comprising fluid flow control elements operated by the computer control system to control and sequence the flows of liquids to the analyzer inlet line.

3. An automated standards sampling apparatus according to claim 1 wherein the connection system of part (e) comprises interconnected fluid sensing, information reading, sequencing and flow control elements providing data to the control system of part (f).

4. An automated standards sampling apparatus according to claim 3 further comprising an electrical connection network connecting the respective sensing, information reading, sequencing and flow control elements.

5. An automated standards sampling apparatus according to claim 1 wherein the fluid connection system of part (e) further comprises at least a sample needle, an associated fluid conduit connected to the at least one sample needle, and at least a vent needle for each vial receiving structure of the standards vial receiving assembly of part (d).

6. An automated standards sampling apparatus according to claim 5 wherein said sample needle and said vent needle are arranged in a coaxial needle configuration whereby a needle end pierces a piercable septum of a standards vial of a standards vial assembly when the standards vial assembly is inserted into the standards vial receiving assembly and thereby fluidically connects the interior of the vial with the associated fluid conduit.

7. An automated standards sampling apparatus according to claim 1 wherein the stream selection element of part (b), the online sample inlet and the associated conduit of part (c), and the fluid connection system of part (e) have interior surfaces that contact a portion of the liquid sample and/or a portion of a standard liquid during use and also wherein all such interior surfaces that contact a liquid that is being analyzed prior to analysis are fabricated from substantially inert materials.

8. An integrated liquid analysis unit comprising an automated standards sampling apparatus according to claim 1 in combination with a liquid analyzer.

9. An integrated liquid analysis unit comprising an automated standards sampling apparatus according to claim 1 in combination with a TOC analyzer.

10. A system for automated standards sampling comprising an integrated liquid analysis unit according to claim 8 in combination with a plurality of standards vial assemblies adapted for insertion into the standards vial receiving assembly, each one of such standards vial assemblies comprising a plurality of standards vials and a vial holding structure that holds the vials in a fixed relationship relative to one another.

11. A system for automated standards sampling comprising an integrated liquid analysis unit according to claim 9 in combination with a plurality of standards vial assemblies adapted for insertion into the standards vial receiving assembly, each one of such standards vial assemblies comprising a plurality of standards vials and a vial holding structure that holds the vials in a fixed relationship relative to one another.

12. A system according to claim 10 wherein each standards vial assembly of the plurality of standards vial assemblies further comprises an information-perceiving and communicating system containing information about the standards vial assembly as a whole as well as about each individual standards vial in the standards vial assembly.

13. A system according to claim 11 wherein each standards vial assembly of the plurality of standards vial assemblies further comprises an information-perceiving and communicating system containing information about the standards vial assembly as a whole as well as about each individual standards vial in the standards vial assembly.

14. A system according to claim 12 wherein said information-perceiving and communicating system is an electronic memory storage device.

15. A system according to claim 13 wherein said information-perceiving and communicating system is an electronic memory storage device.

16. A system according to claim 12 wherein said information-perceiving and communicating system is a bar code-reading device.

17. A system according to claim 13 wherein said information-perceiving and communicating system is a bar code-reading device.

18. A system according to claim 12 further wherein each individual standards vial of a standards vial assembly contains a different standard liquid.

19. A system according to claim 13 further wherein each individual standards vial of a standards vial assembly contains a different standard liquid.

20. A system according to claim 10 wherein each standards vial assembly of the plurality of standards vial assemblies is keyed to the standards vial receiving assembly of the automated standards sampling apparatus by means of a physical feature.

21. A system according to claim 11 wherein each standards vial assembly of the plurality of standards vial assemblies is keyed to the standards vial receiving assembly of the automated standards sampling apparatus by means of a physical feature.

22. A system according to claim 10 wherein the spacing between two adjacent standards vials of a standards vial assembly of the plurality of standards vial assemblies is a different spacing than the spacing between other adjacent vials of the standards vial assembly, and further wherein that different spacing of the standards vial assembly corresponds to a different spacing between corresponding vial receiving structures of the standards vial receiving assembly of the automated standards sampling apparatus.

23. A system according to claim 11 wherein the spacing between two adjacent standards vials of a standards vial assembly of the plurality of standards vial assemblies is a different spacing than the spacing between other adjacent vials of the standards vial assembly, and further wherein that different spacing of the standards vial assembly corresponds to a different spacing between corresponding vial receiving structures of the standards vial receiving assembly of the automated standards sampling apparatus.

24. An automated standards sampling apparatus according to claim 1 wherein said stream selection element of part (b) comprises a hub valve having multiple fluid inlets connecting to the common interior region of the stream selection element and having a hub fluid outlet from the common interior region.

25. A system comprising an automated standards sampling apparatus according to claim 24 and a liquid fluid analyzer, wherein the hub fluid outlet is connected to a first end of the analyzer inlet line of part (a), and the other end of the analyzer inlet line is connected to the liquid analyzer.

26. A system comprising an automated standards sampling apparatus according to claim 24 and a TOC analyzer, wherein the hub fluid outlet is connected to a first end of the analyzer inlet line of part (a), and the other end of the analyzer inlet line is connected to the TOC analyzer.

27. An integrated liquid analysis unit comprising an automated standards sampling apparatus according to claim 2 in combination with a liquid analyzer.

28. An integrated liquid analysis unit comprising an automated standards sampling apparatus according to claim 3 in combination with a liquid analyzer.

29. An integrated liquid analysis unit comprising an automated standards sampling apparatus according to claim 4 in combination with a liquid analyzer.

30. An integrated liquid analysis unit comprising an automated standards sampling apparatus according to claim 5 in combination with a liquid analyzer.

31. An integrated liquid analysis unit comprising an automated standards sampling apparatus according to claim 6 in combination with a liquid analyzer.

32. An integrated liquid analysis unit comprising an automated standards sampling apparatus according to claim 7 in combination with a liquid analyzer.

33. An integrated liquid analysis unit comprising an automated standards sampling apparatus according to claim 2 in combination with a TOC analyzer.

34. An integrated liquid analysis unit comprising an automated standards sampling apparatus according to claim 3 in combination with a TOC analyzer.

35. An integrated liquid analysis unit comprising an automated standards sampling apparatus according to claim 4 in combination with a TOC analyzer.

36. An integrated liquid analysis unit comprising an automated standards sampling apparatus according to claim 5 in combination with a TOC analyzer.

37. An integrated liquid analysis unit comprising an automated standards sampling apparatus according to claim 6 in combination with a TOC analyzer.

38. An integrated liquid analysis unit comprising an automated standards sampling apparatus according to claim 7 in combination with a TOC analyzer.

39. A method of operating an automated standards sampling apparatus for delivering an online flowing liquid sample to an analyzer inlet line, and for alternatively periodically coupling into the apparatus a plurality of standards vials contained in a standards vial assembly seated in a vial receiving portion of the apparatus comprising vial receiving members so as to individually deliver a portion from each of two or more vials in the standards vial assembly in a predetermined sequence to the analyzer inlet line, or instead to deliver a portion of another liquid to the analyzer inlet line, said method comprising the steps of:
(a) providing an analyzer inlet line;
(b) providing a single functional stream selection element having a plurality of stream selection fluid inlets, each being in fluid communication with a common interior region of the stream selection element and wherein the interior region of the stream selection element communicates with the analyzer inlet line of part (a);
(c) flowing an online flowing liquid sample into the apparatus through an online sample inlet and then to one of the stream selection fluid inlets through an online sample conduit when the apparatus is operating in an online mode of operation;
(d) periodically operating in a system suitability testing mode including the steps of stopping the flow of online flowing liquid sample into the stream selection element and coupling into the stream selection element, one at a time, through separate stream selection fluid inlets, and in a predetermined sequence, two or more standards vials contained in a properly coupled standards vial assembly so as to individually deliver a standards portion from two or more of said vials to the analyzer inlet line of part (a), wherein said standards vial assembly comprises a keying feature that is keyed to a corresponding keying feature of the apparatus that prevents the standards vials of the standards vial assembly from being coupled into the stream selection element unless the standards vial assembly is adapted to be used with the sampling apparatus and is correctly oriented to insure proper sequencing of the standards portions;
(e) providing a system of fluid flow control elements to control the flow of liquids into the stream selection element; and,
(f) providing a computer information reading and control system for automatically operating the apparatus so as to deliver the online flowing liquid sample to the analyzer inlet line of part (a) when in the online mode of operation or, alternatively, so as to deliver in a predetermined sequence standards portions from two or more standards vials contained in the coupled standards vial assembly to the analyzer inlet line of part (a) when in the system suitability testing mode.

40. A method according to claim 39 wherein the automated standards sampling apparatus couples to the standards vials contained in a coupled standards vial assembly by a plurality of needle assemblies, whereby each needle assembly pierces a piercable septum of a standards vial, and by a conduit associated with each needle assembly to provide a fluid flow path between the interior of a standards vial and a stream selection fluid inlet.

41. A method according to claim 40 wherein each needle assembly comprises at least a sample needle and at least a vent needle.

42. A method according to claim 41 wherein said sample needle and said vent needle are arranged in a coaxial needle configuration.

43. A method according to claim 39 further wherein flow control elements operated by the computer control system of part (f) control and sequence the flow of liquids to the analyzer inlet line of part (a).

44. A method according claim 39 wherein said system of fluid flow control elements of part (e) comprises interconnected fluid sensing, information reading, sequencing and flow control elements providing data to the control system of part (f).

45. A method according to claim 44 wherein said computer information reading and control system of part (f) further comprises an electrical connection network connecting the respective sensing, information reading, sequencing and flow control elements.

46. A method according to claim 39 wherein the stream selection element of part (b), the online sample inlet and the online sample conduit of part (c), and the stream selection fluid inlets of part (d) have interior surfaces that are contacted by a portion of the liquid sample and/or a portion of a standard liquid during use, further comprising the step of only contacting a liquid sample and/or a standard liquid, prior to analysis, with such interior surfaces that are fabricated from substantially inert materials.

47. A method according to claim 39 wherein a vial holding structure of a standards vial assembly retains the individual standards vials in a fixed relationship relative to one another.

48. A method according to claim 39 further comprising a plurality of standards vial assemblies wherein each standards vial assembly of the plurality of standards vial assemblies comprises an information-perceiving and communicating system containing information about the standards vial assembly as a whole as well as about each individual standards vial in the standards vial assembly.

49. A method according to claim 48 wherein said information-perceiving and communicating system is an electronic memory storage device.

50. A method according to claim 48 wherein said information-perceiving and communicating system is a bar code-reading device.

51. A method according to claim 48 wherein each standards vial of a standards vial assembly contains a different standard liquid.

52. A method according to claim 39 wherein a standards vial assembly is keyed to the automated standards sampling apparatus by means of a physical feature.

53. A method according to claim 52 wherein the spacing between two adjacent standards vials of a standards vial assembly is a different spacing than the spacing between other adjacent vials of the standards vial assembly, and further wherein that different spacing of the standards vial assembly corresponds to a different spacing between corresponding vial receiving members of the automated standards sampling apparatus.

54. A method according to claim 39 further comprising the step of connecting the analyzer inlet line of part (a) to a fluid analyzer.

55. A method according to claim 39 further comprising the step of connecting the analyzer inlet line of part (a) to a TOC analyzer.

* * * * *